United States Patent [19]

Dutcher et al.

[11] Patent Number: 5,217,028

[45] Date of Patent: * Jun. 8, 1993

[54] BIPOLAR CARDIAC LEAD WITH DRUG ELUTING DEVICE

[75] Inventors: Robert G. Dutcher; John C. Hill; Robert J. Scott, all of Minneapolis, Minn.

[73] Assignee: Possis Medical, Inc., Minneapolis, Minn.

[*] Notice: The portion of the term of this patent subsequent to Sep. 1, 2009 has been disclaimed.

[21] Appl. No.: 912,321

[22] Filed: Jul. 13, 1992

Related U.S. Application Data

[60] Continuation-in-part of Ser. No. 707,681, May 30, 1991, Pat. No. 5,143,090, which is a continuation-in-part of Ser. No. 600,627, Oct. 22, 1990, Pat. No. 5,040,545, which is a division of Ser. No. 430,596, Nov. 2, 1989, Pat. No. 4,972,847.

[51] Int. Cl.⁵ .............................................. A61N 1/05
[52] U.S. Cl. ..................................... 128/785; 128/642; 128/790; 128/419 P
[58] Field of Search ............... 128/784, 785, 786, 790, 128/419 P, 642

[56] References Cited

U.S. PATENT DOCUMENTS

| | | | |
|---|---|---|---|
| 4,010,758 | 3/1977 | Rockland et al. | 128/419 P |
| 4,502,492 | 3/1985 | Bornzin | 128/785 |
| 4,506,680 | 3/1985 | Stokes | 128/786 |
| 4,577,642 | 3/1986 | Stokes | 128/784 |
| 4,606,118 | 8/1986 | Cannon et al. | 29/825 |
| 4,711,251 | 12/1987 | Stokes | 128/784 |
| 4,750,977 | 6/1988 | Marrese | 204/27 |
| 4,784,161 | 11/1988 | Skalsky et al. | 128/785 |
| 4,819,661 | 4/1989 | Heil, Jr. et al. | 128/786 |
| 4,819,662 | 4/1989 | Heil, Jr. et al. | 128/786 |
| 4,844,099 | 7/1989 | Skalsky et al. | 128/785 |
| 4,953,564 | 9/1990 | Berthelsen | 128/784 |
| 4,972,848 | 11/1990 | DiDomenico et al. | 128/785 |
| 5,002,067 | 3/1991 | Berthelsen et al. | 128/786 |
| 5,003,992 | 4/1991 | Holleman et al. | 128/642 |
| 5,085,218 | 2/1992 | Heil, Jr. et al. | 128/785 |

Primary Examiner—Kyle L. Howell
Assistant Examiner—George Manuel
Attorney, Agent, or Firm—Burd, Bartz & Gutenkauf

[57] ABSTRACT

A bi-polar cardiac lead for transmitting electric current to the heart and/or sensing and monitoring electrical activity of the heart has elongated electrical conductors connected to a head. The lead has a first electrode mounted on the head having a helical wire connected to one conductor adapted to be turned into heart tissue. The helical wire is coated with platinum black particles which decrease electrical losses at the electrode-tissue interface. A second annular electrode having an irregular outer surface configuration is mounted on the head around the first electrode. A plug impregnated with a drug is located within a recess in the head adjacent the electrodes. The drug migrates from the plug to the stimulation site.

34 Claims, 5 Drawing Sheets

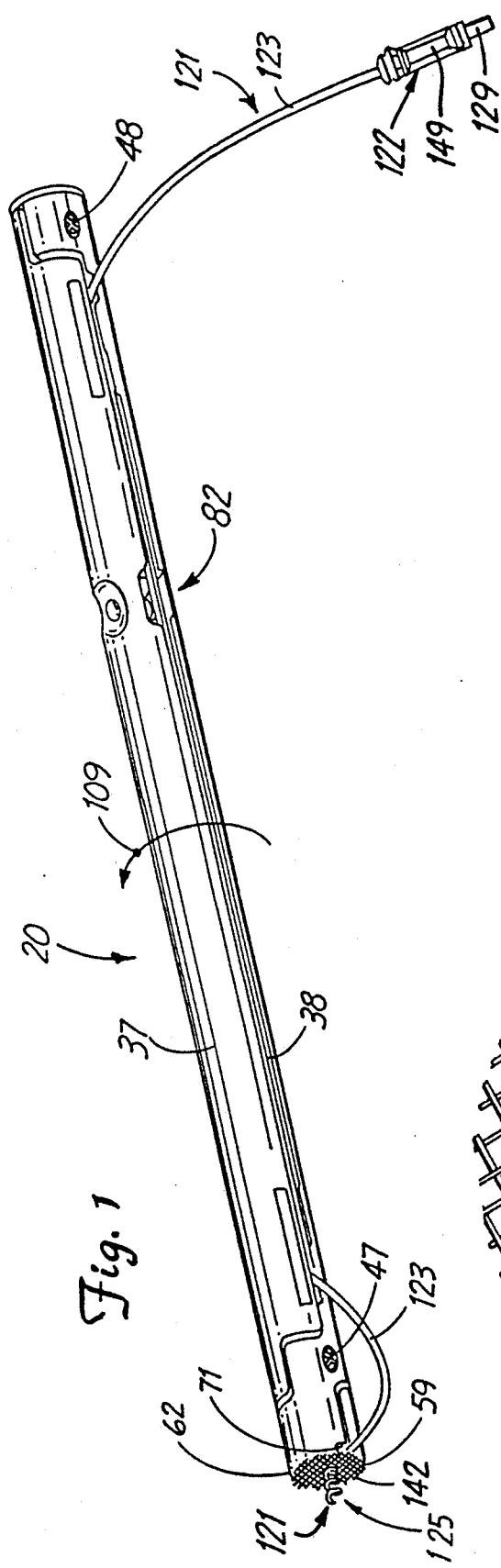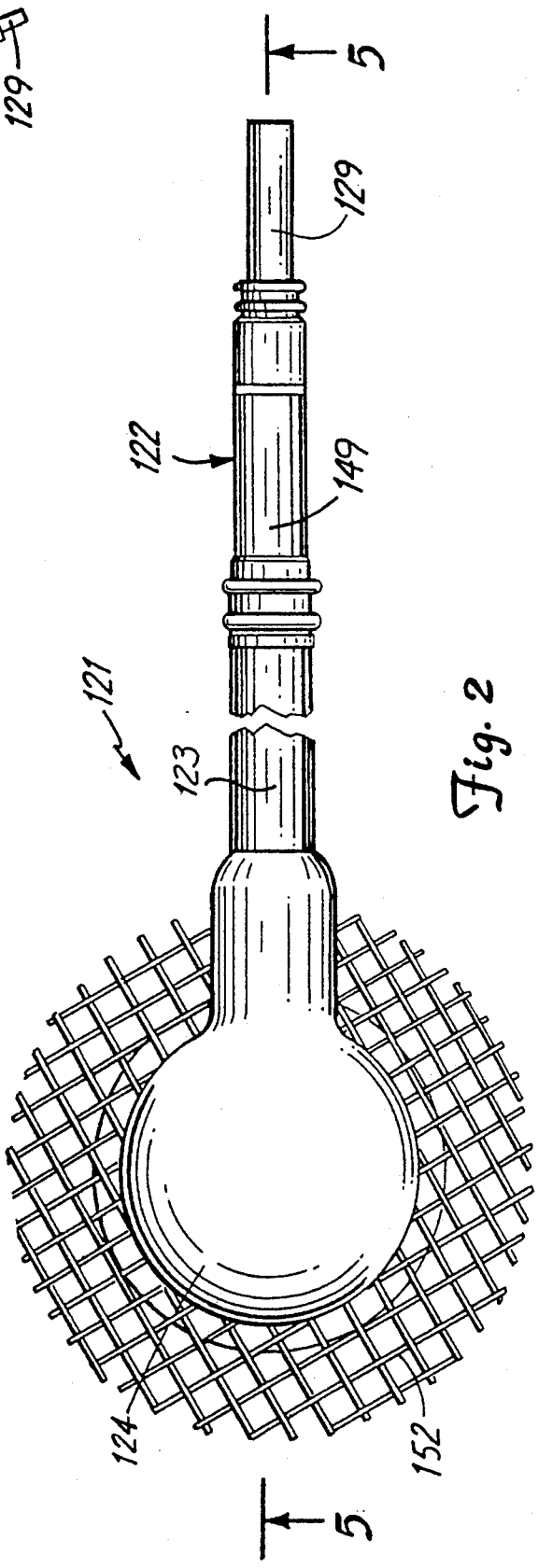

BIPOLAR CARDIAC LEAD WITH DRUG ELUTING DEVICE

CROSS REFERENCE TO RELATED APPLICATION

This application is a continuation-in-part of U.S. application Ser. No. 707,681 filed May 30, 1991, now U.S. Pat. No. 5,143,090. Application Ser. No. 707,681 is a continuation-in-part of U.S. application Ser. No. 600,627 filed Oct. 22, 1990, now U.S. Pat. No. 5,040,545. Application Ser. No. 600,627 is a division of U.S. application Ser. No. 430,596 filed Nov. 2, 1989, now U.S. Pat. No. 4,972,847.

FIELD OF INVENTION

The invention relates to cardiac leads connectable to a heart for transmitting electric signals to the heart and monitoring the electrical activity of the heart. The cardiac leads have devices that dispense steroids or other drugs adjacent the stimulation site.

BACKGROUND OF THE INVENTION

A myocardial lead having a rigid helical coil adapted to be turned into heart tissue is disclosed by L. R. Bolduc in U.S. Pat. No. 3,737,579. The helical coil is a wire connected with an elongated flexible conductor to a pacemaker for transmitting electrical pacing currents to the heart. Interactions between the coil and the heart tissue can reduce the effects of the electrical stimulation. Fibrosis can occur around the coil which increases the chronic threshold and can result in trauma of the heart tissue to be stimulated. The configuration of the electrode can reduce mechanical trauma and minimize fibrosis. Thrombus formation can also be reduced by the administration of suitable drugs to the stimulation site. The delivery of a steroid drug to the stimulation site of an implantable pacing lead is disclosed by W. A. Berthelsen in U.S. Pat. No. 4,953,564. A controlled drug release device is integrated with the fixation helix such that as the helix is extended the controlled drug release device is concurrently extended. The controlled drug release device is limited to the immediate vicinity of the distal end of the helix to minimize the dispersion of the drug into the blood stream. The controlled drug release device has a porous elution path for accommodating the dispensing steroid.

A bi-polar cardiac electrode having a helical electrode and an annular electrode is disclosed by R. H. Rockland and D. H. Gobeli in U.S. Pat. No. 4,010,758. The annular electrode has a flat surface adapted for intimate contact with heart tissues so that a relatively intense electrical field is established through the heart tissue between the helical electrode and the annular electrode. A drug release device is not used with this bi-polar electrode.

SUMMARY OF THE INVENTION

The invention relates to a bi-polar cardiac lead connectable to an implantable cardiac arrhythmia management device (not shown) for transmitting electric current to the heart and/or sensing and monitoring the electrical activity of the heart. The implantable cardiac arrhythmia management device includes but is not limited to cardiac pacemakers and automatic implantable cardiac defibrillators (AICD). The lead has elongated flexible conductors enclosed within a sheath of non-electrically conductive material to electrically connect the cardiac management device with first and second electrodes adapted to be implanted in or on heart tissue. The electrodes are supported on a head of non-electrically conductive material and joined to the conductors. A drug release device mounted in the head provides a source of a drug for elution at the stimulation site.

In one form of the invention the first electrode is a helical wire having a portion located externally of the head adapted to be turned into the heart tissue to secure the electrode to the heart tissue and transmit electrical signals thereto or receive electrical signals therefrom. The helical wire has an inner end extended into the head to support the wire on the head. The wire has at least one helical coil projected away from the generally flat face of the head. A sheath of non-electrically conductive material surrounds the outer end of the wire adjacent the head except for a distal portion thereof which represents the electrode. The external portion of the electrode has an outer surface covered with a layer of platinum black particles. Other types of coatings can be applied to the wire to carry a drug from a source of the drug in the head to the electrode. The sheath covers the coating on the wire except for the distal portion thereof. The layer of platinum black particles has generally uniform particle size and particle distribution on the outer surface of the wire. The platinum black particles on the distal portion of the electrode has a microporous outer surface in contact with the heart tissue which decreases electrical losses at the electrode-tissue interface, establishes intimate contact between the electrode and myocardial tissue, lowers stimulation thresholds, and increases amplitude of electrical signals from the myocardium. The second electrode has an annular electrical conductor secured to the head and extended around the helical wire and source of the drug. The annular conductor has an irregular external surface configuration engagable with the heart tissue around the helical wire. In one form of the invention the second electrode has a member having concentric rings separated with grooves and spokes joined to the rings which form the irregular external surface configuration that engages the heart tissue.

A plug of material that accommodates a drug, such as a steroid, is mounted in the head within the confines of the base of the helical wire. The plug is a cylindrical member coaxially aligned with the longitudinal axis of the helical electrode. The base has a generally cylindrical recess or pocket surrounded by the inner end section of the helical wire. A portion of the wire may be exposed to the pocket. The plug of material, such as silicone rubber, porous glass, ceramic, plastic or metal, or elastic absorbant material, such as cellulose or natural sponge, is located in the pocket in the head and secured to the head. The drug in the plug migrates from the plug into the heart tissue toward the distal end of the electrode wire. The drug is dispensed at the stimulation site to augment the function of stimulation as well as reduce inflammation, fibrotic tissue formation, thrombus formation and arrhythmias. The steroid is incorporated into the material of the plug and in use elutes out of the material in the presence of body fluid. The drug can be incorporated into plastic material of the plug during the polymerization process. Other types of coatings including but not limited to Pyrolytic carbon, titanium nitride, and other surfaces can be used to enhance the electrotissue interface between the electrode and heart tissue and carry the drug to the distal end of the helical wire for dispensing at the stimulation site.

DESCRIPTION OF DRAWING

FIG. 1 is a perspective view of a cardiac lead insertion tool holding an implantable bi-polar cardiac lead;

FIG. 2 is an enlarged foreshortened top plan view of the bi-polar cardiac lead shown in FIG. 1.

DESCRIPTION OF PREFERRED EMBODIMENTS

Referring to FIG. 1, there is shown the myocardial lead installation tool known as an introducer, indicated generally at 20, holding a cardiac lead, indicated generally at 121, prior to the implantation of the lead into the myocardium of a heart. Introducer 20 is disclosed in U.S. Pat. No. 4,972,847, incorporated herein by reference. Lead 121 has a connector 122 at the proximal end thereof adapted to be connected to the terminal of a cardiac management device (not shown) operable to generate heart pacing currents. Connector 122 is joined to an elongated flexible electrical conductor 123 having a distal end joined to a generally cylindrical head 124. Head 124 is made of non-electrical conductive material that is bicompatible, such as medical grade silicone rubber. A rigid helical electrode, indicated generally at 125, having several convolutions is mounted on the center of head 124. Electrode 125 projects outwardly from the central portion of head 124 to enable the outer section thereof to be turned into the myocardium.

Figure 5:
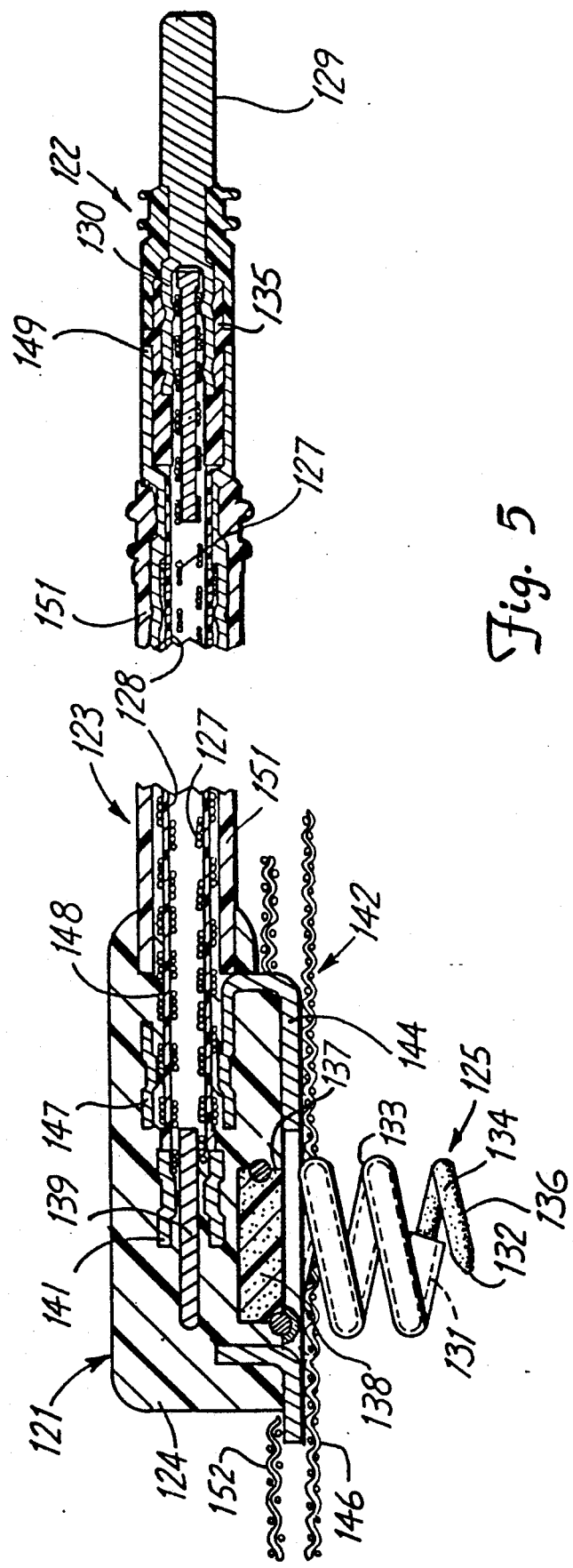
FIG. 5 is an enlarged sectional view taken along line 5—5 of FIG. 2.

As shown in FIG. 5, electrode 125 has an inner end section 126 embedded in head 124 and connected to a first conductor wire 127 of conductor 123. Wire 127 is a multifilar electrical conductor coil made of nickel cobalt wire or other suitable conducting material. Wire 127 is enclosed within non-electrical conductive tube 128 that is biocompatible, such as medical grade silicone rubber. The connector 122 has a collar 130 joined to wire 127. A plastic sleeve 135 surrounds collar 130 to insulate connector male member 129 from a sleeve conductor 149.

Figure 4:
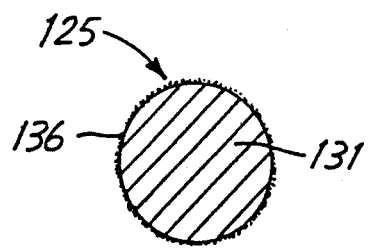
FIG. 4 is an enlarged sectional view taken along line 4—4 of FIG. 3.

Helical electrode 135 is a rigid helical wire 131 terminating in a pointed or sharpened end 132. A sheath 133 of non-electrical conductive material, such as medical grade silicone rubber, covers the helical wire 131 except for about the end one half turn portion 134 thereof, such as between 190 and 190 degrees of the end portion of the wire. End portion 134 of the helical wire comprises the active electrode. Wire 131 has an inner end 139 joined to conductor 127. A sleeve 141 located around end 139 retains the end of conductor 127 on wire end 139. The helical wire 131 can be made of a platinum-/iridium. The entire exterior surface of the end one half turn section of wire 131 is completely covered with a coat or layer of platinum black particles 136 to substantially reduce electrode polarization and facilitate the dispensing of a drug to the stimulation site. Wire 131 is platinized to develop the coating of platinum black particles 136. The entire wire 131 is coated with a generally continuous layer of platinum black particles 136 as shown in FIGS. 4 and 5. The platinum black particles 136 have a micro-porous surface of submicron size particles. The layer of platinum black particles 136 is electrochemically plated onto the outer surface of the wire 131. Wire 131 is placed in a platinum ion plating solution and subjected to an electric d.c. current. The plating solution and wire 131 are also subjected to intermittent ultrasonic vibrations that agitate the platinum ions. The electric current is terminated during the vibration period. The time period between vibration episodes can be varied. An oscillating piezoelectric ceramic is used to generate vibrations at a selected frequency that produces generally uniform particle size and particle distribution. The submicron size particles of platinum black particles 136 bonded to the entire outside surface of the outer end portion 134 of wire 131 up to sheath 133. The platinum black particles 136 have generally uniform particle size and particle distribution resulting in uniform current density over the layer of platinum black particles 136 and lower stimulation thresholds. The current carried by lead 121 is delivered to the heart muscle almost exclusively through the platinum black particles 136 at the outer end 134 of wire 131 as the remainder of wire is covered with sheath 133 and head 124. The layer of platinum black particles 136 has a microporous surface which provides for intimate contact between the end portion 134 of electrode 125 with the myocardial tissue and an increase in real surface area with a resulting decrease in electrode-tissue interface electrical losses and maximize voltage applied to the stimulatable tissue of the heart and thereby lower stimulation thresholds and increase intracardiac electrical signal sensing. The layer of platinum black particles 134 on wire 131 aids in the movement of a drug from a drug source 138 in head 124 to the stimulation site. Other types of materials can be located on wire 131 to enhance the electrical tissue interface between the active electrode and the heart tissue and facilitate the dispensing of a drug t the stimulation site.

As shown in FIG. 5, the mid-section of the inner side of head 124 has a cylindrical recess or pocket 137 accommodating a plug 138 impregnated with a drug to elution at the stimulation site. Plug 138 is secured to head 124 with suitable bonding material. The inner end section 126 of wire 131 is turned around the outer circumference of plug 138 to locate plug 138 in co-axial alignment with helical electrode 125. The drug will be dispensed from the outer surface of plug 138 to the heart tissue as plug 138 positioned in contacting relationship with the heart tissue.

Plug 138 is a solid cylindrical one-piece plastic member, such as polyurethane, impregnated with a drug having an axis coaxially aligned with the longitudinal axis of helical electrode 125. Other types of materials including but not limited to silicone rubber, porous glass, porous ceramic, porous metal and like bio-compatable materials can be used for pug 138 to accommodate one or more drugs.

Examples of the drug incorporated into the material of plug 138 include steroids, such as glucocorticosteroids, and sodium salt of dexamethasone phosphate. Other drugs that can be incorporated into plug 138 are disclosed by Di Domenico et. al. in U.S. Pat. No. 4,972,848, incorporated herein by reference.

A second annular electrode 142 or anode surrounds the helical cathode electrode 125 and plug 138. A netting 152 joined to head 124 surrounds lower end of head 124 and extends radially outwardly therefrom to increase the surface area engagement of electrode 142 with the epicardium. Electrode 142 has non-flat surfaces locatable in intimate electrical contact with heart tissue. Netting 152 is a porous polyester fiber that enhances fibrotic growth. The inner portion of netting 152 is secured to the head 124 to insure a secure contact of electrodes 125 and 142 and plug 138 of the heart tissue.

Figure 3:
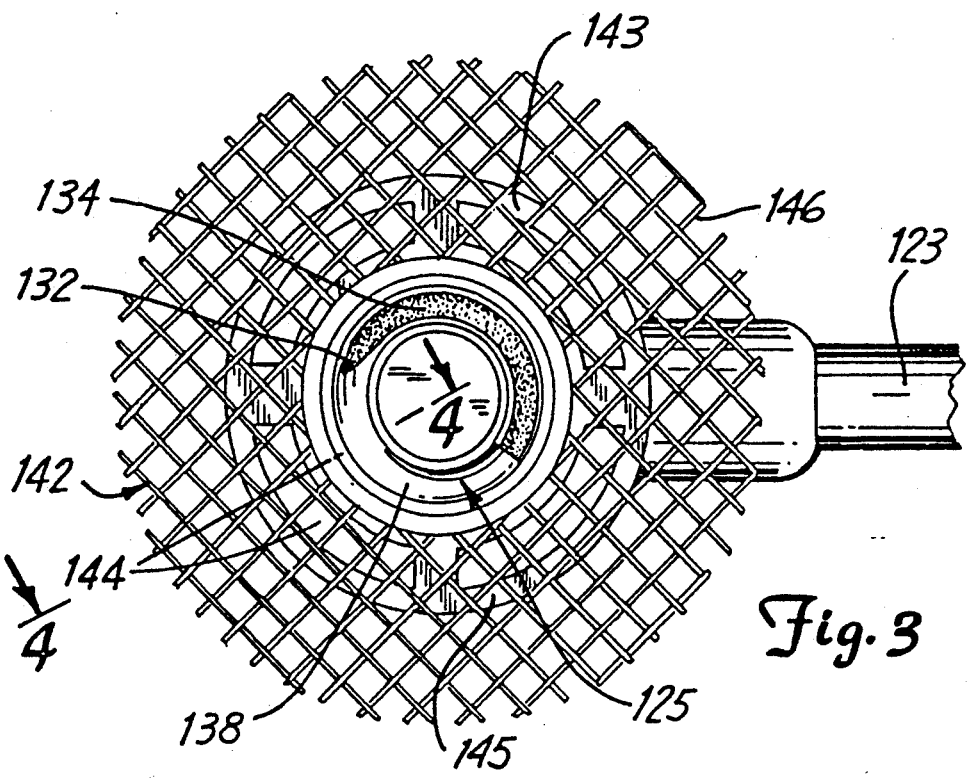
FIG. 3 is an enlarged bottom plan view of the distal end of the bi-polar cardiac lead of FIG. 2.

As shown in FIGS. 3 and 5, second electrode 142 includes a support or washer-like member 144 attached to the bottom of head 124. Support 144 has a pair of concentric rings 143 and 145 joined with generally radial spokes. Support 144 can be titanium that is joined or bonded to porous electrode 146. Electrode 146 has a non-flat surface shown as a wire mesh. The wire mesh may be platinum wire mesh or titanium wire mesh coated with platinum black particles. Ring 143 projects radially outward from the base of head 124 to provide annular support for electrode 146. Support 144 has an upwardly directed tab embedded in the material of head 124. Diametrically opposite of the tab is an upwardly directed ear terminating in a generally cylindrical sleeve 147 concentric with and laterally spaced outwardly from insulation tube 128.

A second conductor coil 148 surrounds tube 128. Coil 148 has a proximal end located within a metal conductor sleeve 149. A flexible sleeve or tubular member 151 is located around the outside of a section of sleeve 149 whereby sleeve 149 is a second conductor. Coil 148 is surrounded with outer flexible silicone rubber member 151 of non-electrically conductive medical grade rubber which is located over part of tube 149 and connected to head 124. A sleeve 147 located in engagement with coil 148 provides an electrical connection between tube 149 and second electrode 146.

Returning to FIG. 1, introducer 20 has a pair of elongated beams 37 and 38 pivotally connected at their opposite ends with pivot members 47 and 48. The distal ends of beams 37 and 38 have a pair of arcuate jaws 59 and 62 for gripping opposite sides of head 124 of lead 121. Beams 37 and 38 have a slot 71 adjacent jaws 59 and 62 which allows conductor 123 to be located between beams 37 and 38. A releasable lock mechanism, indicated generally at 82, holds beams 37 and 38 to a closed position to maintain the gripping force of jaws 59 and 62 on head 124. Releasable lock mechanism 82 can be disengaged to allow beams 37 and 38 to move to an open position releasing the grip of jaws 59 and 62 on head 124. Introducer 20 is rotated in the direction of the arrow 109 during the implant procedure of helical electrode 125. Only a small keyhole opening in the chest wall is requested to implant the lead. The detailed structure and operation of introducer 20 is disclosed in U.S. Pat. No. No. 1,972,847, incorporated herein by reference. Porous electrode 146 and plug 138 are retained in intimate surface contact with the heart tissue. The electrode 146 and netting 152 being porous enhances tissue in growth to firmly fix head 124 to the heart tissue.

Referring to FIGS. 6 to 9, there is shown a modification of the bi-polar cardiac lead indicated generally at 221. Lead 21 has an elongated flexible coaxial conductor 222 having a connector (not shown) such as connector 122 shown in FIGS. 2 and 5. Conductor 222 has the same structure as conductor 121 shown in FIGS. 1, 2 and 5. Lead 221 has a head 224 supporting a first electrode 225, a second electrode 242 and netting 252. Head 224 has cylindrical body 214 of biocompatable material, such as silicone rubber, surrounding the inner end of electrode 225. Body 214 has a lateral member 223 secured to conductor 222 having an outer cylindrical rubber cover 251.

Figure 8:
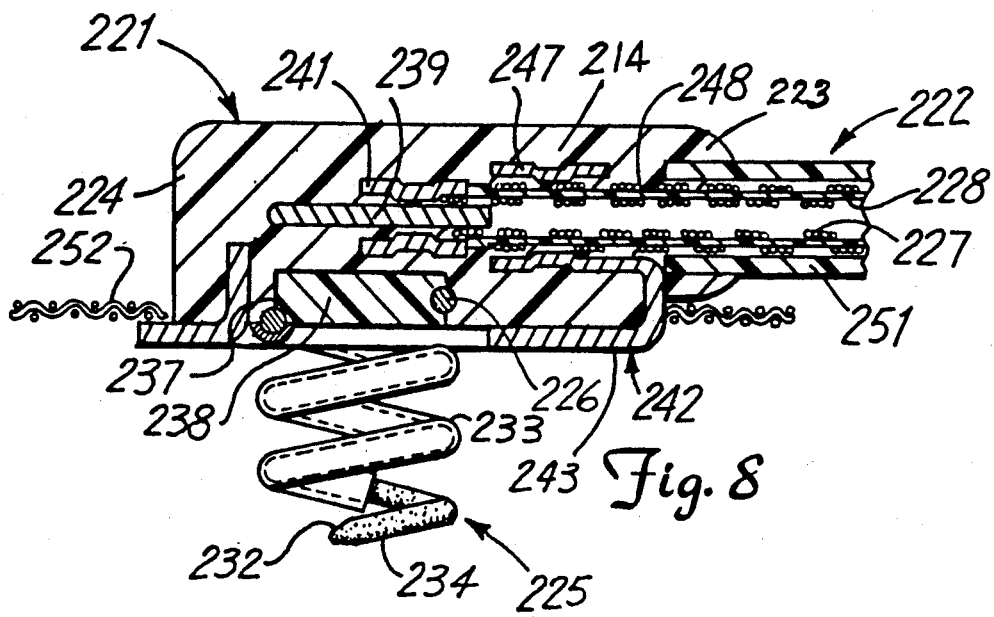
FIG. 8 is a sectional view taken along line 8—9 of FIG 6.

Electrode 225 has a helical wire 226, such as a platinum or platinum iridium wire, having an exposed outer end portion 234 terminating in a sharp point 232. Outer end portion 234 of electrode 225 is covered with a coating of platinum black particles. The coating or layer of platinum black particles has a generally uniform particle size and distribution over the outer surface of the outer end portion 234 which in use is placed in a microscopic surface contact with the heart tissue. This decreases the electrical losses and increases the amplitude of electrical signals from the myocardium. A portion of electrode 25 from head 224 to end 234 is enclosed within a sheath or coating 233 of medical grade rubber which electrically insulates this portion of the wire from the heart tissue. As shown in FIG. 8, the inner end of electrode 225 is embedded within head 24 and is in electrical engagement with a first or inner conductor coil 227. Coil 227 is in contact with a sleeve 241 embedded within head 224. A pin 239 located within coil 227 holds coil 227 in engagement with sleeve 241. Pin 239 can be at the end of the wire of electrode 225. Head 224 has a recess or pocket 237 open to the bottom or inner side thereof. Recess 237 has a cylindrical shape to accommodate a cylindrical plug 238. Plug 238 is a solid cylindrical one-piece plastic member, such as polyurethane, impregnated with a drug, such as a steroid. Other drugs can be incorporated in plug 238 as described herein with reference to plug 138. The inner end of helical wire 226 surrounds plug 238. An adhesive is used to secure plug 238 to head 224. Plug 238 has an outer circular surface exposed to heart tissue adjacent electrode 225 and surrounded by second electrode 242 whereby drug eludes from plug 238 to the heart tissue at the stimulation site.

Figure 7:
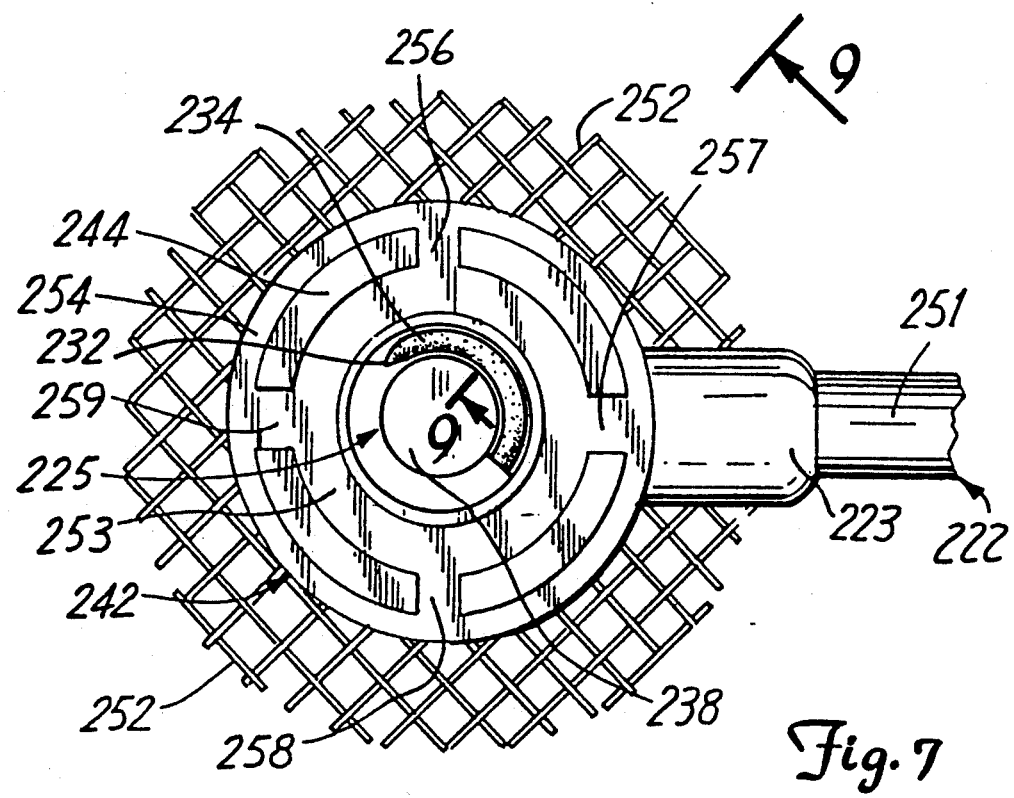
FIG. 7 is a bottom plan view f the distal end of the bi-polar cardiac lead of FIG. 6.
Figure 9:
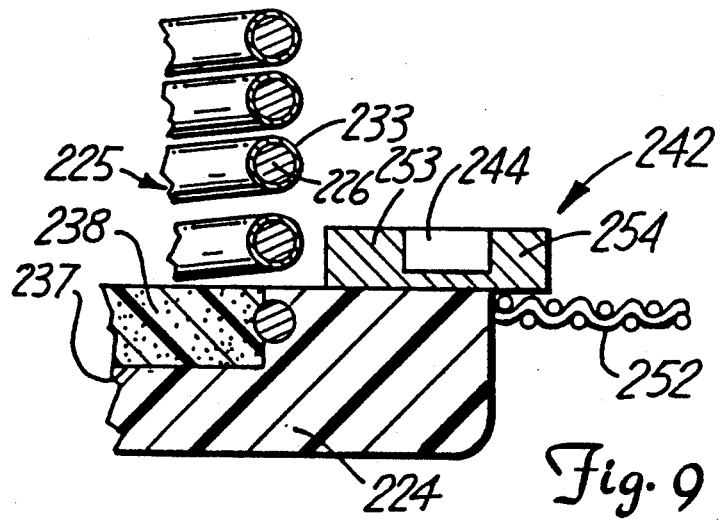
FIG. 9 is an enlarged sectional view taken along line 9—9 of FIG. 7.

As shown in FIGS. 7, 8 and 9, second electrode indicated generally at 242 is an anode mounted on the bottom of head 224. Electrode 242 is a toroidal metal electrode member 243 having stepped outer surfaces adapted to engage the heart tissue. The entire outer surface of the electrode member is not flat thereby providing increased surface area as compared to a flat surface. Electrode 242 has a pair of concentric rings 253 and 254 connected with radial spokes 256-259. Spokes 256-259 are separated from each other with segment or arcuate grooves 244. As shown in FIG. 7, four circumferentially spaced grooves 244 are open to the outside or contact surface of electrode 242. Other types of irregular or non-flat surfaces can be used with electrode 242 to increase the surface area of contact between electrode 242 and the heart tissue. The bottom surfaces of the grooves 244 can be coated with platinum black particles. The coating can be platinum or iridium. All of the outer surfaces of electrode 242 can be coated with platinum black particles, platinum or iridium. Other surface treatments including but not limited to Pyrolite carbon and titanium nitride can be used to enhance the electro-tissue interface between the second electrode 242 and heart tissue.

Figure 6:
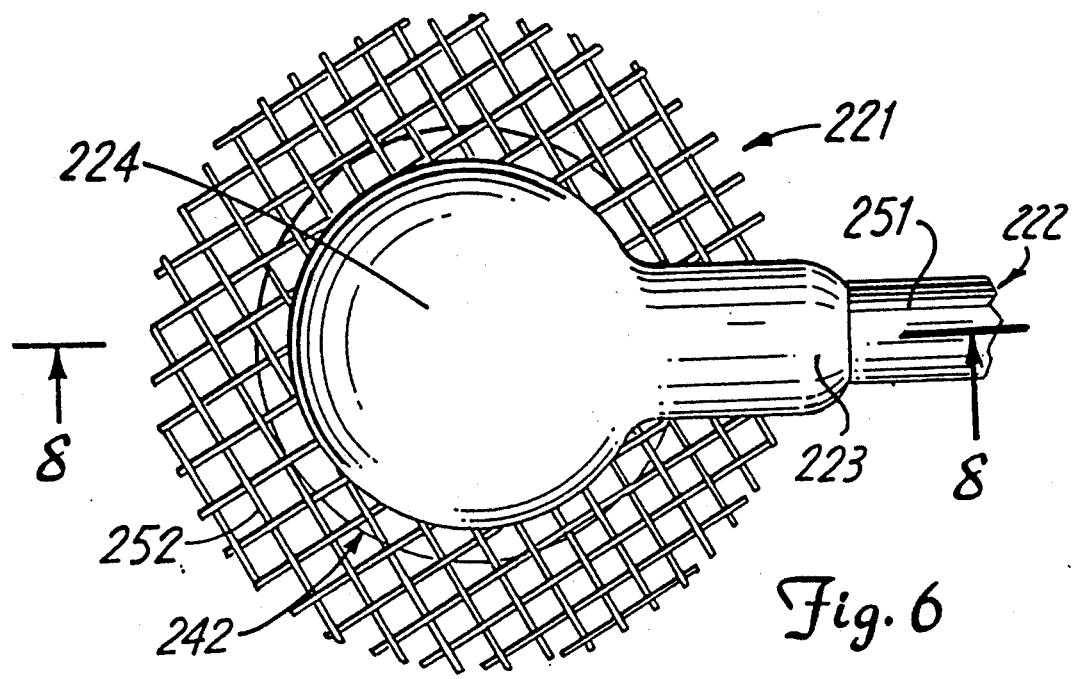
FIG. 6 is a top plan view of the distal end of a modification of the bi-polar cardiac lead.

An upwardly directed tab embedded in head 224 is joined to one side of ring 253 aligned with spoke 259. Diametrically opposite the tab is an upwardly directed ear joined to a sleeve 247 surrounding the distal end of conductor coil 248. Second coil 248 located about an insulation or rubber tube 228 surrounding first coil 227 fits into sleeve 247. An expansion insert (not shown) located about the plastic tube 228 holds second coil 248 in engagement with sleeve 247 thereby electrically connecting second coil 248 with second electrode 242. As shown in FIGS. 6 and 8, electrode 242 has a diameter greater than the diameter of head 224. An outer peripheral annular portion of electrode 242 extends radially outwardly from head 224. Electrode 242 is made of titanium or like conductive biocompatible materials having a coating of platinum black particles or a coating of platinum or iridium. The non-flat outside surface construction of electrode 242 increases the surface contact area with a heart tissue and provides for effective sensing vector in all directions.

The dispensing of a steroid drug at the stimulation site is enhanced by the drug migrating to the porous coating of platinum black particles at the outer end of the electrode 225. The drug augments the function of stimulation and reduces the pacing and sensing thresholds. The drug also reduces irritability and fibros formation and minimizes other electrode related problems including inflammation and arrhythmias. The current carried by lead is delivered to the heart muscle almost exclusively through platinum black particles and the micro-porous surface of the platinum black particles is in intimate contact with the myocardial tissue. The presence of the steroid drug in the micro-porous surface lowers stimulation thresholds and increases cardiac electrical signal sensing.

While there have been shown and described preferred embodiments of the cardiac lead of the invention. It is understood that changes in the structure, arrangement of structure and materials may be made by those skilled in the art without departing from the invention. The invention is defined in the following claims.

We claim:

1. A cardiac lead connectable to a cardiac management device for transmitting electric current to and/or receiving electrical signals from the myocardium of the heart comprising: an elongated flexible conductor wire means, sheath means of non-electrical conductive material surrounding said conductor wire means, an electrical connector attached to the wire means adapted to be connected to a cardiac management device, a head of non-electrically conductive material connected to said conductor wire means and sheath means, a helical first electrode having a first end section extended into said head and connected to said conductor wire means and a helical second end section extended from said head adapted to be screwed into the myocardium of a heart, said second end section having an outer helical surface terminating in a point, a layer of platinum black particles attached to the outer helical surface of the second end section, said layer of platinum black particles having generally uniform particle size and distribution on said outer surface of the second end section of the electrode whereby said layer has a microporous outer platinum black surface locatable in surface contact with the myocardium of the heart whereby said layer of platinum black particles decreases electrical losses at the electrode-tissue interface, establishes intimate contact between the electrode and myocardium, and maximizes voltage applied to said myocardium and lowers stimulation thresholds and increases amplitude of sensed electrical signals from the myocardium, means carrying a drug mounted on the head for supplying the drug to the myocardium of the heart, a second electrode including a porous wire mesh secured to the support means surrounding the helical electrode engagable with the myocardium of the heart around the helical electrode when the helical electrode is attached to the myocardium, support means holding the second electrode on the head, and a second elongated flexible conductor wire connected to the support means located within the sheath means and electrically insulated from the first elongated flexible conductor wire means adapted to be connected to the cardiac management device.

2. The lead of claim 1 wherein: said head has a recess adjacent the helical first electrode, and said means carrying a drug being located in said recess.

3. The lead of claim 2 wherein: the recess has a generally cylindrical shape, and said means carrying a drug comprises a plastic plug having a size and shape to fill the recess.

4. The lead of claim 3 wherein: said plug has an axis aligned with the longitudinal axis of the helical first electrode.

5. The lead of claim 1 including: porous means secured to the head surrounding said helical second end section to enhance fibrotic growth to connect the head to the myocardium.

6. The lead of claim 1 including: sheath means of non-electrically conductive material extended from said head covering a portion of the helical second section of said electrode, said second section having an end portion projected from said sheath means, said end portion having an outer surface covered with said platinum black particles.

7. The lead of claim 1 wherein: the support means comprises an electrical conductor attached to the head, said electrical conductor having an irregular surface configuration adapted to engage heart tissue, said support means surrounding said means carrying a drug mounted on the head.

8. The lead of claim 7 wherein: the electrical conductor is an annular member having an exterior surface having at least one groove.

9. A cardiac lead connectable to a cardiac management device for transmitting electric current to a heart and/or receiving electrical signals from the heart comprising: an elongated flexible conductor means, sheath means of non-electrically conductive material surrounding said conductor means, an electrical connector attached to the conductor means adapted to be connected to a cardiac management device, a head of non-electrical conductive material connected to said conductor means and sheath means, a first electrode means having a first section extended into said head and connected to said conductor means and a second section extended from said head adapted to be placed in engagement with heart tissue, said second section having an end portion with an outer surface, means carrying a drug mounted on the head for supplying the drug to the myocardium of the heart, and a second electrode means surrounding the first electrode connected to said conductor means, said second electrode means having an outer surface adapted to contact heart tissue when the second section of the first electrode is in engagement with heart tissue, said outer surface of the second electrode means having an irregular surface configuration, the second electrode means comprises an annular support means of electrically conductive material secured to the head, and a porous wire mesh conductor secured to the support means.

10. The lead of claim 9 wherein: said head has a recess adjacent the helical first electrode, and said means carrying a drug being located in said recess.

11. The lead of claim 10 wherein: the recess has a generally cylindrical shape, and said means carrying a drug comprises a plastic plug having a size and shape to fill the recess.

12. The lead of claim 11 wherein: said plug has an axis aligned with the longitudinal axis of the helical first electrode.

13. The lead of claim 9 including: porous means secured to the head to enhance fibrotic growth to connect the head to the myocardium.

14. The lead of claim 9 including: sheath means of non-electrically conductive material extended from said head covering a portion of the helical second section of said electrode, said second section having an end portion projected from said sheath means, said end portion having an outer surface covered with platinum black particles.

15. The lead of claim 9 wherein: the annular support means has spaced concentric rings, a plurality of circumferentially spaced spokes connected to the rings and a plurality of grooves located between the rings.

16. The lead of claim 9 wherein: the first electrode has a first end section extended into the head and a second helical end section adapted to be screwed into the myocardium of the heart.

17. The lead of claim 9 wherein: the wire mesh conductor has a coating of platinum black particles, platinum, Pyrolite carbon or titanium nitride.

18. A cardiac lead connectable to a cardiac management device for transmitting electric current to a heart and/or receiving electrical signals from the heart comprising: an elongated flexible conductor means, sheath means of non-electrically conductive material surrounding said conductor means, an electrical connector attached to the conductor means adapted to be connected to a cardiac management device, a head of non-electrical conductive material connected to said conductor means and sheath means, a first electrode means having a first section extended into said head and connected to said conductor means and a second section extended from said head adapted to be placed in engagement with heart tissue, said second section having an end portion with an outer surface, means carrying a drug mounted on the head for supplying the drug to the myocardium of the heart, and a second electrode surrounding the first electrode connected to said conductor means, said second electrode having an outer surface adapted to contact heart tissue when the second section of the first electrode is in engagement with heart tissue, said outer surface of the second electrode having an irregular surface configuration larger than the outer surface of the conductor means.

19. The lead of claim 18 wherein: said head has a recess adjacent the helical first electrode, and said means carrying a drug being located in said recess.

20. The lead of claim 19 wherein: the recess has a generally cylindrical shape, and said means carrying a drug comprises a plastic plug having a size and shape to fill the recess.

21. The lead of claim 18 wherein: said plug has an axis aligned with the longitudinal axis of the helical first electrode.

22. The lead of claim 18 wherein: the irregular surface configuration of the second electrode includes a member having spaced concentric rings, at least one spoke connected to the rings, and a plurality of grooves located between the rings, said irregular surface configuration comprising outer surfaces of the rings and spoke and surfaces at the base of the grooves.

23. The lead of claim 22 wherein: the member has a plurality of circumferentially spaced spokes connected to the rings.

24. The lead of claim 18 including: means on at least one of the surfaces of the first and second electrodes to enhance the electrical tissue interface between the surfaces of the first and second electrodes and heart tissue.

25. The lead of claim 24 wherein: the means to enhance the electrical tissue interface includes a coating of platinum black particles, platinum, Pyrolite carbon, or titanium nitride.

26. A cardiac lead connectable to a cardiac management device for transmitting electric current to and/or receiving electrical signals from the myocardium of the heart comprising: an elongated flexible first conductor means adapted to be connected to the cardiac management device, sheath means of non-electrically conductive material surrounding said conductor means, a head of non-electrically conductive material attached to the conductor means and sheath means, a helical first electrode having a first end section extended into said head and connected to said conductor means and a helical second end section extended from said head adapted to be screwed into the myocardium of a heart, means carrying a drug mounted on the head for supplying the drug to the myocardium of the heart, a second electrode secured to the head surrounding the helical first electrode, said second electrode including a member of electrically conductive material having spaced concentric rings and at least one spoke connected to the rings having first outer surfaces and grooves between the rings, said member having second outer surfaces at the bases of the grooves, said first and second outer surfaces being engagable with the myocardium of the heart around the helical electrode when the helical electrode is screwed into the myocardium, and a second elongated flexible conductor means conductively connected to said second electrode located within the sheath means and electrically insulated from the first conductor means.

27. The lead of claim 26 wherein: said head has a recess adjacent the helical first electrode, and said means carrying a drug being located in said recess.

28. The lead of claim 27 wherein: the recess has a generally cylindrical shape, and said means carrying a drug comprises a plastic plug having a size and shape to fill the recess.

29. The lead of claim 28 wherein: said plug has an axis aligned with the longitudinal axis of the helical first electrode.

30. The lead of claim 26 including: porous means secured to the head surrounding said helical second end section to enhance fibrotic growth to connect the head to the myocardium.

31. The lead of claim 26 including: sheath means of non-electrically conductive material extended from said head covering a portion of the helical second section of said electrode, said second section having an end portion projected from said sheath means, said end portion having an outer surface covered with said platinum black particles.

32. The lead of claim 26 including: means on the second end section of the helical first electrode to enhance the electrical tissue interface between the second end section and the heart tissue.

33. The lead of claim 32 wherein: the means to enhance the electrical tissue interface including a coating of platinum black particles, platinum, Pyrolite carbon, and titanium nitride.

34. The lead of claim 26 including: a fabric netting secured to the head to enhance fibrotic growth to secure the head to the heart tissue.

* * * * *